(12) United States Patent
Antonelli et al.

(10) Patent No.: US 8,064,060 B2
(45) Date of Patent: Nov. 22, 2011

(54) OUTBOARD OPTICAL CABLE SENSOR SYSTEM AND METHOD

(75) Inventors: Lynn T. Antonelli, Cranston, RI (US); Armando M. Simao, Pawcatuck, CT (US); Donald I. Woodward, Wakefield, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 126 days.

(21) Appl. No.: 12/730,398

(22) Filed: Mar. 24, 2010

(65) Prior Publication Data
US 2011/0235040 A1 Sep. 29, 2011

(51) Int. Cl.
*G01N 21/31* (2006.01)
(52) U.S. Cl. ........................................................ 356/435
(58) Field of Classification Search ........................ None
See application file for complete search history.

(56) References Cited

U.S. PATENT DOCUMENTS

| | | | | |
|---|---|---|---|---|
| 4,266,874 A | * | 5/1981 | Janin et al. | 356/335 |
| 4,600,874 A | * | 7/1986 | Tupper et al. | 318/798 |
| 5,174,033 A | * | 12/1992 | Rider | 177/45 |

* cited by examiner

*Primary Examiner* — Tu Nguyen
(74) *Attorney, Agent, or Firm* — James M. Kasischke; Jean-Paul A. Nasser; Michael P. Stanley

(57) ABSTRACT

A plurality of optical sensors are mounted to a housing made of optically conductive material. The housing seals the optical sensors from a water-filled tube which extends through said housing. The optically conductive material provides optical coupling with the water-filled cable tube whereby a plurality of light beams are directed through the housing and the water-filled tube in a predetermined pattern, which provides certainty of the absence or presence of a cable within the water-filled cable tube for a minimum cable diameter regardless of the orientation of the cable within the water-filled tube.

10 Claims, 3 Drawing Sheets

OUTBOARD OPTICAL CABLE SENSOR SYSTEM AND METHOD

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER PATENT APPLICATIONS

None.

BACKGROUND OF THE INVENTION

1. Field of the Invention

The present invention relates generally to remote sensors and, more particularly, to an optical sensor system to detect the presence and absence of a towed array cable within a submarine's water-filled cable tube.

2. Description of the Prior Art

The currently available outboard sensor assembly utilized in many submarines to detect a thin-line towed array employs an acoustic sensor to alert the system operator of one of two conditions for the water-filled cable tube, either "tube empty" or "tube full." The acoustic sensors require open access to the tube's water-filled environment for efficient acoustic coupling into the tube. The open access requires cutting out section of the tube, which is a leak risk factor for submarine safety. Because of the location of the outboard sensor assembly on a submarine, the repair and replacement is problematic. Moreover, acoustic sensors have been found to be unreliable, which has led to the continual refit of submarines coming out of the shipyards.

The following U.S. patents describe various prior art systems that may be related to the above and/or other MFC power conditioners:

U.S. Pat. No. 4,518,862 teaches an apparatus for determining the position of a sheet when the sheet is placed on a support having at least two spaced apart CCD linear image sensors recessed in the sheet support and partially covered by the edge portions of the sheet. The CCDs operate as line cameras, and are scanned to generate signals correlated with the points of intersection of the sheet edges and the axes of the image sensors. Preferably the apparatus has circuitry for storing calibration values of the CCD signals obtained when the image sensors are not covered by the sheet, circuitry for storing corresponding scanning signal values when the image sensors are covered by the sheet, circuitry for comparing corresponding calibration and scanning values for obtaining difference values, and circuitry for detecting maxima in the gradient of the difference values for adjacent image points to find the locations of the points of intersection of the sheet edges and the axes of image sensors. These locations are used by software driving an X-Y plotter head or by a sheet positioning mechanism to correct for variations in sheet position.

U.S. Pat. No. 5,406,092 discloses semiconductor wafer-detecting apparatus provided with a main support body formed of synthetic resin. A pair of substantially-parallel longitudinal channels and a plurality of substantially-parallel transverse channels are formed in the main support body. The longitudinal channels are located away from each other by a predetermined distance, and the transverse channels are arranged at intervals corresponding to the intervals at which wafers are arranged. Between the adjacent transverse channels, a plurality of pairs of holding portions are defined such that each pair is associated with the longitudinal channels. A pair of light-emitting elements and a pair of light-receiving elements are alternately arranged with reference to the holding portions. The light-emitting elements of each pair have their light-emitting faces oriented in opposite directions; likewise, the light-receiving elements of each pair have their light-receiving faces oriented in opposite directions. The light-emitting elements of each pair and associated light-receiving elements jointly constitute respective optical sensors. The presence or absence of a wafer is determined by detecting whether or not light is shielded between the light-emitting and light-receiving elements of each optical sensor.

U.S. Pat. No. 5,440,391 teaches a device for determining a position with respect to a reference plane of at least one lead of an electronic component, wherein the lead is illuminated from a first and respectively second position situated sideways and out of the plane wherein the electronic component is disposed and wherein a first and respectively a second shadow image is formed of at least a part of the lead on an image plane, which second position is different from the first position and wherein the first and respectively the second shadow image is located and a third and respectively a fourth position is determined to this end and the position is determined from the third and fourth position.

U.S. Pat. No. 5,501,633 teaches a coin mechanism having a coin storage tube and an optical sensor for sensing the level of coins in the tube, the sensor comprising a light source arranged to direct a light beam across the tube, a reflector for returning the beam across the tube and a light detector for detecting the returned beam is disclosed. The reflector for returning the beam is a concave mirror having a curvature such as to give the beam an area, where it approaches the detector, substantially greater than the effective area of the detector. This enables, in a compact sensor, the light intensity at the detector to be enhanced and at the same time the sensitivity to misalignment of components to be reduced.

U.S. Pat. No. 5,701,122 teaches an electronic curb feeler system that uses two pairs of optical sensor units to detect an object located near the front end of a vehicle during parking. One pair of optical sensor units detects an object directly in front of a left portion of the front end of the vehicle while another pair of optical sensors detects an object directly in front of a right portion of the front end of the vehicle. By supplying the operator of the vehicle with the location of the object as well as the exact distance the object is from the front end of the vehicle the operator can avoid hitting the object while parking very close to the object.

U.S. Pat. No. 6,806,947 teaches an apparatus and method for determining the presence of a fluid conduit at a predetermined location and at least one characteristic of the fluid in the conduit are disclosed. The apparatus includes a light source for generating radiated light in a direction towards the predetermined location, such that when the fluid conduit is present at the predetermined location the radiated light passes in a direction through the fluid conduit, a first optical sensor for detecting the radiated light through the fluid conduit, and a second optical sensor for detecting the radiated light which is reflected by the fluid conduit.

U.S. Pat. No. 6,979,814 teaches a multi-optical-path photoelectric safety apparatus that has a light emitting unit, a light receiving unit and a control unit for controlling each optical path. A light block substance sensing function for a multi-optical-path light curtain is also provided to sense an object between the light emitting unit and the light receiving unit. A muting area setting unit is also provided that can be taught how to set an area for exerting a muting function. The muting function can be provided only in a partial area of the light curtain by using the muting area setting unit.

U.S. Pat. No. 7,335,116 teaches an object locating system that detects the presence of an object as it passes through two consecutive planar fields of view. Two pairs of optical sensor arrays with multiple, directed, pixel detectors observe the object from two angles as the object passes through each consecutive field of view. The locations of penetrations of the respective fields of view are calculated by triangulation. Using this data, the known location of the take-off point and/or the delay between penetrations, the trajectory of the object in time and space is calculated. Applications include projecting the range of a driven golf ball, measuring the respective arriving and departing velocities of a hit baseball, and determining the trajectory and origin of an arriving projectile, as in the case of the threat to a military vehicle.

U.S. Pat. No. 7,355,727 teaches a system for checking the position of a mechanical part, for example a tool of a lathe, along a checking direction. The system employs an optoelectronic device with a laser beam and a sensor for detecting the interruption of the beam. Mutual displacements between the part to be checked and the optoelectronic device within a checking area are controlled according to a sequence including linear inspection movements along a direction perpendicular to the checking direction and at inspection positions. The inspection positions are spaced apart along the checking direction at progressively decreasing mutual distances, according to a sequence that converges to the searched position.

The above cited prior art does not disclose an outboard optical sensor system operable for determining the absence or presence of a thin-line towed array cable within a tube.

SUMMARY OF THE INVENTION

One object of the present invention is to provide an improved apparatus and method to detect a relatively small cable within a relatively larger water-filled tube.

A further object of the present invention is to provide a more reliable cable detection sensor system.

Another possible object of the present invention is to provide a cable sensor system that does not require open water access to a water-filled tube.

Another possible object of the present invention is to provide an optical cable detection system which determines whether a water-filled cable tube for a towed array used in a submarine is in a "tube empty" or "tube full" condition.

Accordingly, the present invention provides an optical sensor system for detecting the presence or absence of a cable within a water-filled tube. The cable comprises a cable diameter which is smaller than the water-filled tube. For example, the cable may be less than one-half or one-third of a tube diameter of the water-filled tube.

One embodiment of the optical sensor system may comprise a housing comprising an optically clear material which surrounds the water-filled tube. The housing is optically coupled to the water-filled tube whereby the housing is operable for conducting light into the water-filled tube.

A first optical sensor may comprise a first optical transmitter and a first optical receiver which are mounted to the housing on opposite sides of the water-filled tube so as to be sealed off from the water by the optically clear material. The first optical sensor is operable to direct a first light beam into the water-filled tube and detect the first light beam on the other side of the water-filled tube if the cable does not block the first light beam.

If desired, the optical cable sensor system may comprise a second optical sensor comprising a second optical transmitter and a second optical receiver, which are mounted to the housing on opposite sides of the water-filled tube so as to be sealed off from the water by the optically clear material. The second optical sensor is operable to direct a second light beam into the water-filled tube and detect the second light beam on the opposite side of the tube if the cable does not block the second light beam.

In one embodiment, the optical cable system may utilize a third optical sensor comprising a third optical transmitter and a third optical receiver, which are mounted to the housing on opposite sides of the water-filled tube so as to be sealed off from the water by the optically clear material. The third optical sensor is operable to direct a third light beam into the water-filled tube and detect the third light beam on the other side of the tube if the cable does not block the third light beam.

A detector circuit may be electrically connected to the first optical sensor, the second optical sensor, and the third optical sensor so as to be operable to produce a signal indicative of a presence or absence of the cable within the water-filled tube.

The first optical sensor, the second optical sensor, and the third optical sensor may be angularly offset with respect to each other around a circumference of the water-filled tube.

Each of the first optical sensor, the second optical sensor, and the third optical sensor may be mounted such that the first light beam, the second light beam, and the third light beam are oriented substantially orthogonally with respect to an axis of the water-filled tube.

The first optical sensor, the second optical sensor, and the third optical sensor may be mounted so as to be axially offset from each other with respect to an axis of the water-filled tube.

The first light beam, the second light beam, and the third light beam are comprised of red light or other frequency of light that passes through water without significant attenuation.

The present invention also provides methods for detecting the presence or absence of a cable within a water-filled tube. The method may comprise steps such as providing a housing which surrounds the water-filled tube and providing that at least a portion of the housing comprises an optically clear material to thereby provide optical coupling to the water-filled tube.

Other steps may comprise providing a first optical sensor with a first optical transmitter and a first optical receiver mounted to the housing on opposite sides of the water-filled tube and utilizing the first optical sensor to direct a first light beam through at least a portion of the housing into the water-filled tube.

The method may comprise providing additional sensors such as a second optical sensor with a second optical transmitter and a second optical receiver mounted to the housing on opposite sides of the water-filled tube. Additional steps may comprise utilizing the second optical sensor to direct a second light beam through at least a portion of the housing into the water-filled tube.

Other steps may comprise providing a third optical sensor with a third optical transmitter and a third optical receiver mounted to the housing on opposite sides of the water-filled tube and utilizing the third optical sensor to direct a third light beam through at least a portion of the housing into the water-filled tube.

Other steps may comprise monitoring the first optical sensor, the second optical sensor, and the third optical sensor to produce a signal indicative of a presence or absence of the cable within the water-filled tube.

The method may comprise providing that the first optical sensor, the second optical sensor, and the third optical sensor are positioned angularly offset with respect to each other around a circumference of the water-filled tube.

The method may comprise mounting the first optical sensor, the second optical sensor, and the third optical sensor such that the first light beam, the second light beam, and the third light beam are oriented substantially orthogonally with respect to an axis of the water-filled tube.

The method may further comprise providing that the first optical sensor, the second optical sensor, and the third optical sensor are positioned axially offset from each other with respect to an axis of the water-filled tube.

The method may further comprise utilizing a light frequency which passes through water for the first light beam, the second light beam, and the third light beam.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings, wherein like reference numerals refer to like parts and wherein.

DETAIL DESCRIPTION OF THE INVENTION

Figure 1:
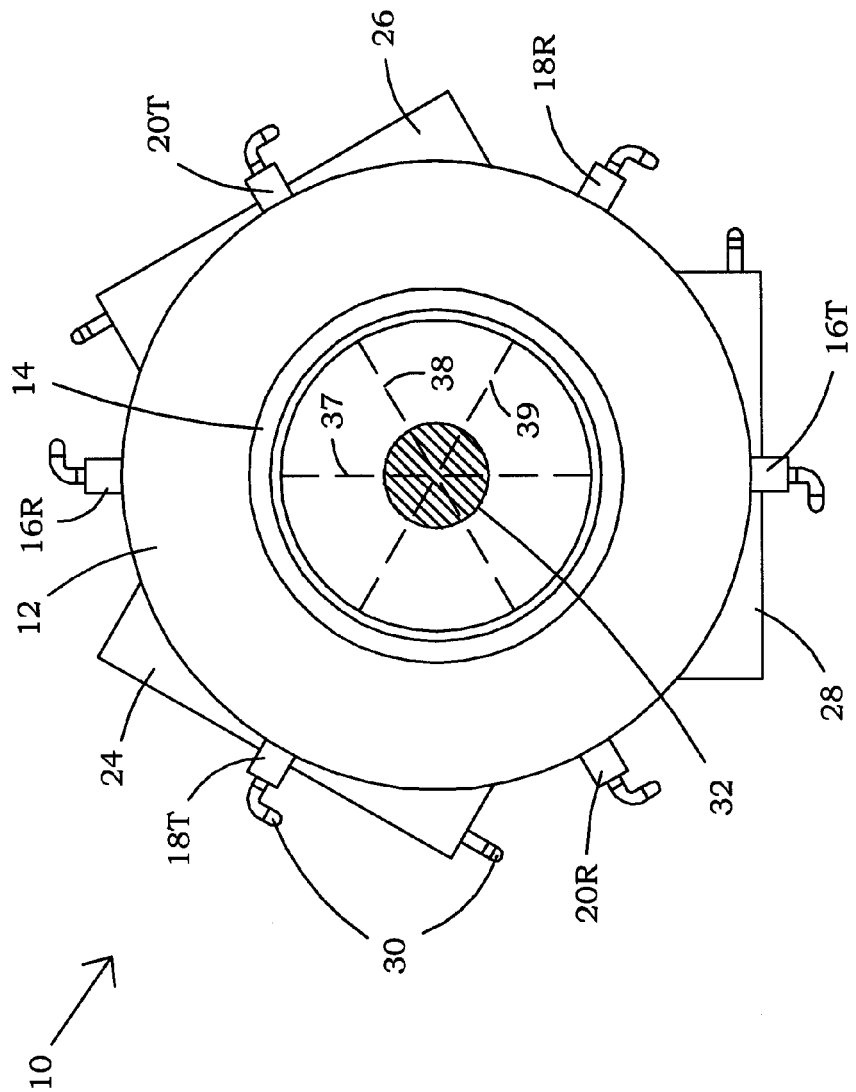
FIG. 1 is an elevational view, partially in section, showing an outboard optical sensor system with three optical transmitter and receiver pairs angularly spaced around a water-filled cable tube in accord with one possible embodiment of the present invention.
Figure 2:
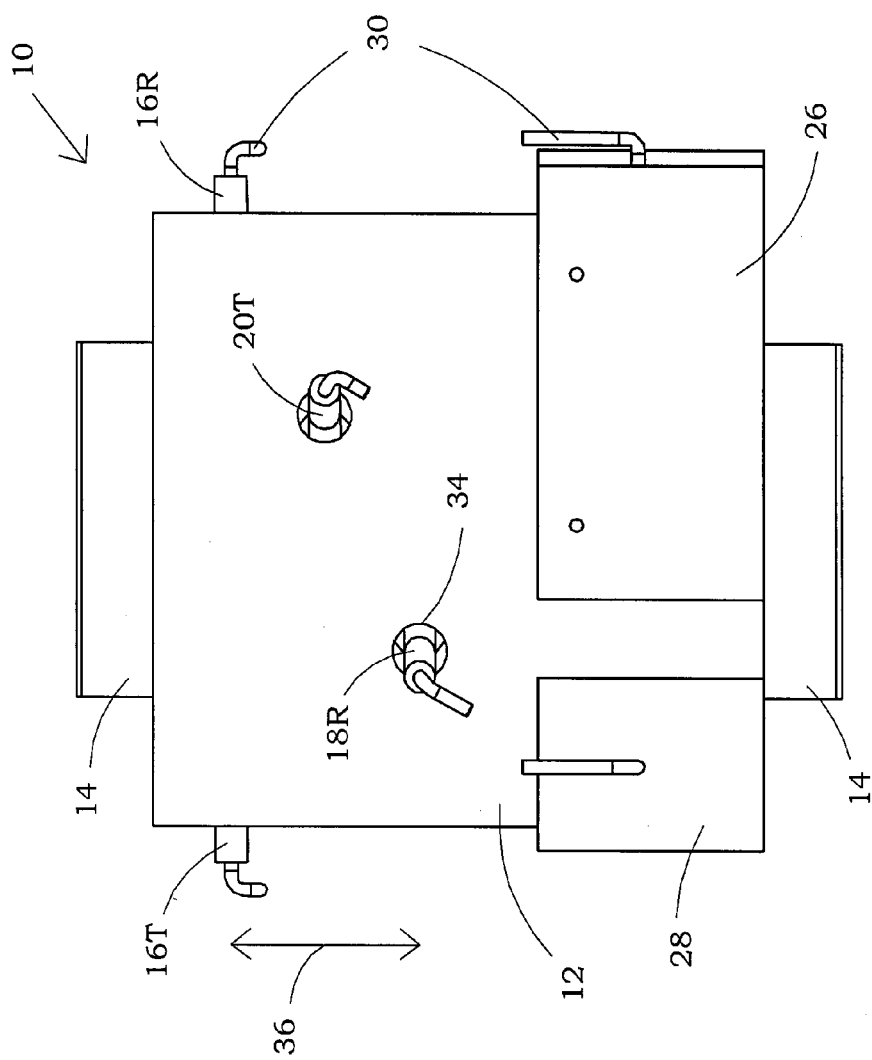
FIG. 2 is a side elevational view of the system of FIG. 1 showing the three optical transmitter and receiver pairs axially spaced along the cable tube in accord with one possible embodiment of the present invention.

Referring now to the drawings and, more particularly, to FIG. 1 and FIG. 2 there is shown optical sensor system 10 in accord with one embodiment of the invention. In this embodiment, three optical sensors are equidistantly angularly spaced around cable tube 14. The three optical sensors produce light beams 37, 38, and 39 which pass through optical material of housing 12, into water-filled cable tube 14, and back into housing 12 where they are detected, assuming the light beams are not blocked by cable 32.

In this embodiment, each optical sensor comprises an optical transmitter and receiver pair. The three optical transmitters comprise optical transmitters 16T, 18T, and 20T. The three corresponding optical receivers comprise optical receivers 16R, 18R, and 20R. In one embodiment, Keyence, model PXH71 optical sensor pairs are utilized. However, other types of suitable optical sensors may also be utilized in accord with the discussion hereinafter.

Figure 3:
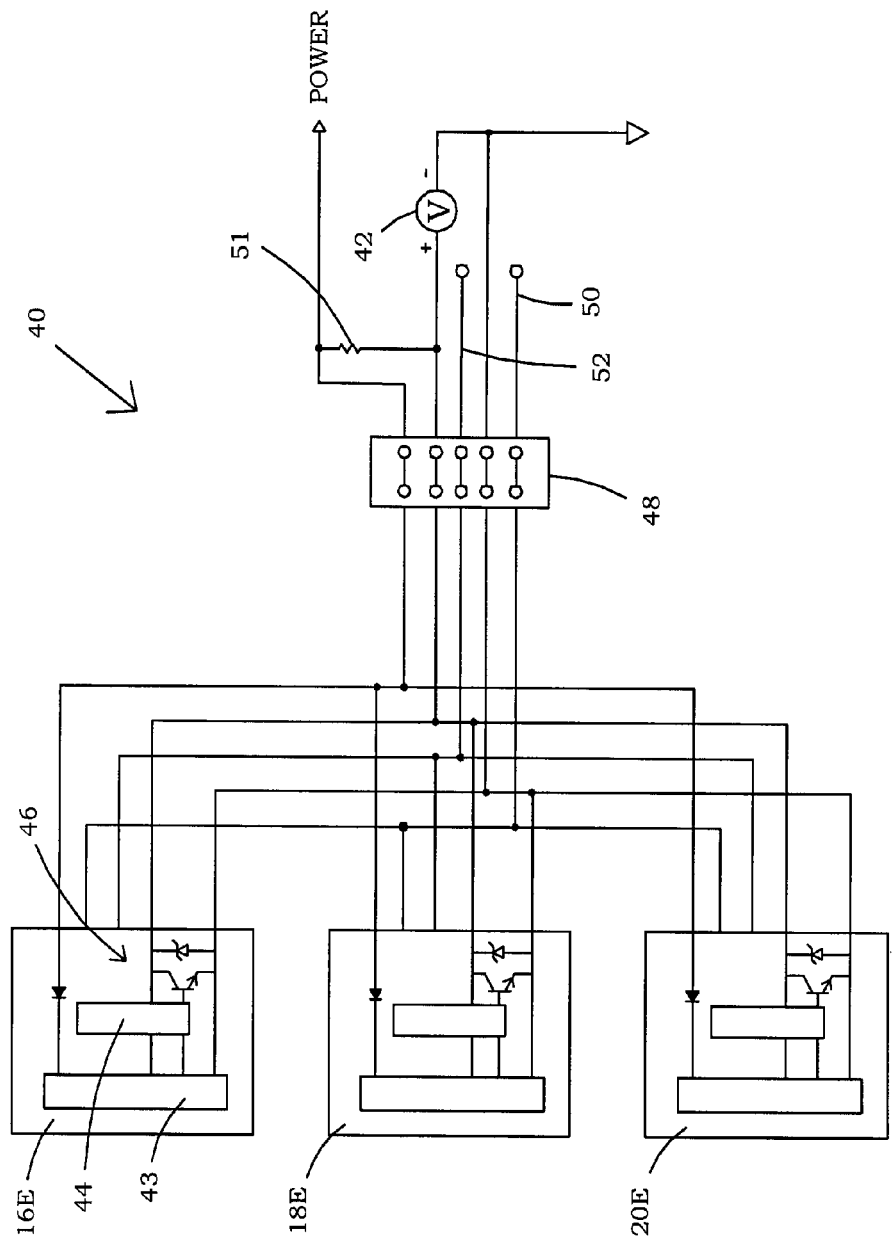
FIG. 3 is an electronic diagram showing circuitry for an outboard optical sensor system in accord with one possible embodiment of the present invention.

Each optical transmitter and receiver pair is connected to a small amplifier device, one possible example of which is indicated as transistor amplifier 46 in FIG. 3. Amplifier 46 provides an output from and is a part of amplifier unit 16E. Suitable amplifier units, such as identical amplifier units 16E, 18E, and 20E control the operation of each optical sensor. The amplifier units preferably allow selection of preset sensor configuration options and contain the input and output electrical lines. Amplifier compartments 24, 26, and 28, which are mounted to housing 12 as shown in FIG. 1 and FIG. 2, may be utilized to house associated amplifier units 16E, 18E, and 20E.

Cables 30, which are only partially shown in FIGS. 1 and 2, extend from the optical transmitter and receiver pairs as well as from amplifier compartments 24, 26, and 28 to provide electrical interconnections therebetween and with terminal block 48 shown in FIG. 3, which may or may not be mounted to housing 12.

As discussed above, the three optical transmitter and receiver pairs are mounted to housing 12, which is comprised of optically clear material, such as clear polycarbonate. Tube 14 is also comprised of optically clear material whereby optical coupling is provided between tube 14 and housing 12. Tube 14 may be defined by or consist of an opening through housing 12. At a minimum, tube 14 is comprised of optically clear material at least where the optical path of the three optical transmitter receiver pairs intersects tube 14. If desired, the outer surface of housing 12 may comprise a metal casing. The optically clear material of housing 12 isolates the optical sensors from the water. Sockets or openings, such as socket 34, may be formed within housing 12 for mounting of the optical sensors.

In this embodiment, each transmitter is angularly spaced around the circumference of cable tube 14 at 120 degrees apart. The corresponding receivers are positioned on the other side of cable tube 14 directly opposite the mating transmitter. In this example, each optical transmitter receiver pair is positioned substantially orthogonally or at a right angle with respect to an axis of tube 14.

The three optical transmitter and receiver pairs 16T, 16R, 18T, 18R, 20T, and 20R may be mounted around cable tube 14 such that the surface area probed by the light beams is capable of detecting the presence of the tow cable at its thinnest dimension as it moves about within the tube. In one embodiment, the three optical transmitter and receiver pairs are organized to effectively produce light rays 37, 38, and 39 which separate the tube into six equal sized pie-shaped sections. The minimum size cable which will be detected by at least one optical transmitter receiver pair regardless of the position of cable 32 within tube 14 can be determined by considering the size of the base of the pie-shaped sections.

For example, if cable tube 14 has a diameter of 2.035 inches, then as long as the diameter of cable 32 is at least 0.685 inches, then cable 32 will be detected no matter where in cable tube 14 it may be positioned. In other words, the smallest cable size that will always be detected utilizing three pairs of optical transmitter receivers can be determined by calculating the maximum cable size that fits within a sixty degree arc angle of the cross-sectional circular outline of the size cable tube which is utilized.

The three optical sensor pairs may preferably also be axially spaced apart from each other as indicated in FIG. 2. For example, distance 36 is that axial spacing between optical transmitter receiver pair 16T, 16R and 18T, 18R. In this example, optical transmitter receiver pair 20T, 20R is positioned between the other sensor pairs.

Each optical sensor operates by transmitting light pulses through housing 12 and from one side of tube 14 to a receiver mounted within housing 12 on the opposite side of tube 14. When cable 32 is not in water-filled tube 14, then the light passes directly through to all three optical transmitter receiver pairs and the detector output provides a high output signal at voltmeter 42 in FIG. 3. In one embodiment, this may be a 15 volt signal. Accordingly, in this embodiment, a relatively high voltage signal is a "tube empty" signal. If the cable is in the tube, then the light is blocked from reaching the receiver of at least one of the optical transmitter receiver pairs and the output detection signal provides a low signal, which in one embodiment may be zero volts or a near zero volt level, e.g., a 5 mV level at voltmeter 42. In this embodiment, the relatively low voltage output signal is a "tube full" signal.

In the electronic circuit diagram of FIG. 3, amplifier units 16E, 18E, and 20E are identical. Accordingly, only amplifier unit 16E is discussed in any detail and it will be understood that the discussion also applies to amplifier units 18E and 20E. Item 43 comprises an optical transmitter receiver pair, such as 16T and 16R, which in this embodiment comprise a Keyence, model PXH71 optical sensor pair, i.e., a photoelectric sensor. Item 44 is an overcurrent protection circuit utilized to protect the optical sensor pair 43. It will be appreciated that instruction manuals for any particular type of commercially available sensor may be utilized in the associated electronic circuitry.

Optical sensor pair 43 provides an electrical signal to output transistor circuit 46. If the cable is detected by optical sensor pair 43, i.e., if the light beam is blocked, then output transistor circuit 46 produces a low output. If the cable is not detected, i.e., if the light beam is not blocked, then the output is high, assuming none of the light beams are blocked.

In this embodiment, output transistor circuit 46 and all other output transistor circuits are connected in parallel across voltmeter 42. If any output transistor circuit produces a low voltage output, i.e., a light beam is blocked, then the output of all three sensor circuits 16E, 18E, and 20E are pulled to a low voltage to thereby indicate cable 32 is detected within water-filled tube 14.

In this embodiment, five wires from each amplifier unit 16E, 18E, and 20E are connected to five terminals of terminal block 48. Terminal block 48 may be mounted to one side of polycarbonate housing 14. Line 52 may be utilized to provide an alarm signal, which indicates a nominal change in the ambient light level, which is calibrated into the "tube empty" and "tube full" voltage outputs. The alarm signal may be used to determine in the inside of the tube needs to be cleaned or that the circuit needs recalibration. In this embodiment, line 50 may be utilized as a reset line to effect the recalibration.

In this embodiment, resistor 50, connects the power to voltmeter 42. The other side of voltmeter 42 is connected to ground. Resistor 50 limits current to one side of voltmeter 42 The relatively low current permitted through resistor 50 allows any transistor output circuit, such as transistor output circuit 46, to pull the voltage across voltmeter 42 to a low value, which indicates the "tube full" condition. Accordingly, all three electronic units 16E, 18E, and 20E have to read the "tube empty" condition before the detection output signal would change from the "tube full" low voltage value to a high voltage level to indicate the "tube empty" condition.

External electronics (not shown) may preferably include an ON/OFF switch, a reset button and indicator LEDs. For example, voltmeter 42 of circuit 40 may provide a signal to the submarine by lighting one or more LEDs indicating "tube empty" and/or "tube full." The ON/OFF switch allows optical sensor assembly 10 to be turned off when it is not needed, such as by turning off the power. The ON/Off switch may also be utilized to erase an alarm indicator if an alarm signal was triggered utilizing line 52. The Reset button may be connected to line 50 and would be used to calibrate or change the light level threshold for determining the "tube empty" or "tube full" conditions.

The optical sensor assembly 10 of the present invention has an estimated lifetime of 80,000 hours (9 years) with anticipated use or a lifetime of 54,000 hours (6 years) with continuous (always on) use.

The optical sensor assembly 10 does not require holes within the mounting structure to allow light energy into the water, eliminating the potential for an internal leak. The light passes through the polycarbonate base with minimal attenuation.

Several variations in the design, components and sensor configuration would be possible while maintaining sensor operability. The brand of laser or photoelectric sensor may vary. The current sensor configuration uses three narrow beam sensors but wider beam sensors may also be utilized.

In this embodiment, red was selected for the light beam frequency since it would pass through polycarbonate housing 12 and the water volume in tube 14. Most visible light colors would also work. Infrared light would be absorbed by the water volume and thus infrared sensors are preferably not utilized.

The number of optical sensors may be varied to detect relatively larger or smaller cables. For example, if a smaller cable is utilized then four sensor pairs, spaced equilaterally, could be utilized. If a larger cable is utilized, then perhaps only one optical sensor could be utilized.

The polycarbonate material was selected since it is the same material currently being used for other outboard sensor assemblies. Other materials may be used in place of the polycarbonate as long as they are sufficiently optically clear to allow the sensor light to propagate through housing 12 without a detrimental affect to the sensors.

The placement of the sensor hardware in the assembly, such as the sensor heads and amplifiers may vary. Accordingly, the shape of sockets 34 in the polycarbonate material of housing 12 would change to accommodate the new sensor hardware configuration.

Many additional changes in the details, components, steps, and organization of the system, herein described and illustrated to explain the nature of the invention, may be made by those skilled in the art within the principle and scope of the invention. It is therefore understood that within the scope of the appended claims, the invention may be practiced otherwise than as specifically described.

What is claimed is:

1. An optical sensor system for detecting the presence or absence of a cable within a water-filled tube, said cable comprising a cable diameter less than one-half of a tube diameter of said water-filled tube, said optical sensor system comprising:

a housing comprising an optically clear material which surrounds said water-filled tube, said housing being optically coupled to said water-filled tube whereby said housing is operable for conducting light into said water-filled tube;

a first optical sensor comprising a first optical transmitter and a first optical receiver which are mounted to said housing on opposite sides of said water-filled tube so as to be sealed off from said water by said optically clear material, said first optical sensor being operable to direct a first light beam into said water-filled tube and detect said first light beam if said cable does not block said first light beam;

a second optical sensor comprising a second optical transmitter and a second optical receiver which are mounted to said housing on opposite sides of said water-filled tube so as to be sealed off from said water by said optically clear material, said second optical sensor being operable to direct a second light beam into said water-filled tube and detect said second light beam if said cable does not block said second light beam;

a third optical sensor comprising a third optical transmitter and a third optical receiver which are mounted to said housing on opposite sides of said water-filled tube so as to be sealed off from said water by said optically clear material, said third optical sensor being operable to direct a third light beam into said water-filled tube and detect said third light beam if said cable does not block said third light beam; and a detector electrically connected to said first optical sensor, said second optical sensor, and said third optical sensor so as to be operable to produce a signal indicative of a presence or absence of said cable within said water-filled tube.

2. The optical sensor system of claim 1, wherein said first optical sensor, said second optical sensor, and said third optical sensor are angularly offset with respect to each other around a circumference of said water-filled tube.

3. The optical sensor system of claim 1, wherein each of said first optical sensor, said second optical sensor, and said third optical sensor are mounted such that said first light beam, said second light beam, and said third light beam are oriented substantially orthogonally with respect to an axis of said water-filled tube.

4. The optical sensor system of claim 1, wherein each of said first optical sensor, said second optical sensor, and said third optical sensor are mounted so as to be axially offset from each other with respect to an axis of said water-filled tube.

5. The optical sensor system of claim 1, wherein each of said first light beam, said second light beam, and said third light beam are comprised of a frequency which passes through water.

6. A method for detecting the presence or absence of a cable within a water-filled tube, said cable comprising a cable diameter less than one-half of a tube diameter of said water-filled tube, said method comprising:

providing a housing which surrounds said water-filled tube;

providing that at least a portion of said housing comprises an optically clear material to thereby provide optical coupling to said water-filled tube;

providing a first optical sensor which comprises a first optical transmitter and a first optical receiver mounted to said housing on opposite sides of said water-filled tube;

utilizing said first optical sensor to direct a first light beam through at least a portion of said housing into said water-filled tube;

providing a second optical sensor comprising a second optical transmitter and a second optical receiver mounted to said housing on opposite sides of said water-filled tube;

utilizing said second optical sensor to direct a second light beam through at least a portion of said housing into said water-filled tube;

providing a third optical sensor comprising a third optical transmitter and a third optical receiver mounted to said housing on opposite sides of said water-filled tube;

utilizing said third optical sensor to direct a third light beam through at least a portion of said housing into said water-filled tube; and monitoring said first optical sensor, said second optical sensor, and said third optical sensor to produce a signal indicative of a presence or absence of said cable within said water-filled tube.

7. The method of claim 6, comprising providing that said first optical sensor, said second optical sensor, and said third optical sensor are positioned angularly offset with respect to each other around a circumference of said water-filled tube.

8. The method of claim 6, comprising mounting said first optical sensor, said second optical sensor, and said third optical sensor such that said first light beam, said second light beam, and said third light beam are oriented substantially orthogonally with respect to an axis of said water-filled tube.

9. The method of claim 6, comprising providing that said first optical sensor, said second optical sensor, and said third optical sensor are positioned axially offset from each other with respect to an axis of said water-filled tube.

10. The method of claim 6, comprising utilizing a light frequency which passes through water for said first light beam, said second light beam, and said third light beam.

\* \* \* \* \*